United States Patent
Popelar et al.

(10) Patent No.: US 9,188,513 B2
(45) Date of Patent: Nov. 17, 2015

(54) SAMPLING DEVICE FOR THERMAL ANALYSIS

(71) Applicant: SinterCast AB, Stockholm (SE)

(72) Inventors: Patrik Popelar, Katrineholm (SE); Steve Wallace, Rejmyre (SE)

(73) Assignee: SinterCast AB, Stockholm (SE)

( * ) Notice: Subject to any disclaimer, the term of this patent is extended or adjusted under 35 U.S.C. 154(b) by 0 days.

(21) Appl. No.: 14/329,486

(22) Filed: Jul. 11, 2014

(65) Prior Publication Data

US 2015/0013478 A1   Jan. 15, 2015

(30) Foreign Application Priority Data

Jul. 12, 2013 (SE) ...................................... 1350874

(51) Int. Cl.
*G01N 1/12* (2006.01)
*G01N 25/04* (2006.01)
*G01N 33/20* (2006.01)
*G01N 1/10* (2006.01)

(52) U.S. Cl.
CPC ............. *G01N 1/125* (2013.01); *G01N 25/04* (2013.01); *G01N 33/206* (2013.01); *G01N 2001/1031* (2013.01)

(58) Field of Classification Search
CPC ..... G01N 1/125; G01N 25/04; G01N 33/206; G01N 2001/1031
USPC .......... 73/863.71, 863.81, 864.51, 866.5, 461
See application file for complete search history.

(56) References Cited

U.S. PATENT DOCUMENTS

| 4,002,073 A | * | 1/1977 | Collins ...................... 73/864.57 |
| 4,074,578 A | | 2/1978 | Collins |
| 4,448,825 A | * | 5/1984 | Asahara ...................... 428/34.7 |
| 5,949,000 A | * | 9/1999 | Lindholm et al. ......... 73/864.91 |
| 6,102,981 A | * | 8/2000 | Lindholm ....................... 75/382 |

(Continued)

FOREIGN PATENT DOCUMENTS

| EP | 1034419 A1 | 9/2000 |
| GB | 1350248 | 4/1974 |

(Continued)

OTHER PUBLICATIONS

Office Action received for Japanese Patent Application No. 2014-132417, mailed on Aug. 25, 2014, 5 pages (3 pages of English Translation and 2 pages of Office Action).

(Continued)

*Primary Examiner* — Peter Macchiarolo
*Assistant Examiner* — Natalie Huls
(74) *Attorney, Agent, or Firm* — Morrison & Foerster LLP

(57) ABSTRACT

A sampling device comprises a container having an essential cylindrical part and a bottom part. The container further comprises an inner wall member and an outer wall member. The inner wall member and the outer wall member are essentially coaxially arranged in the cylindrical part of the container and joined at the top part of the container, and the inner and outer wall members define a closed insulating space between the outer surface of the inner wall member and the inner surface of the outer wall member. The sampling device further comprises temperature responsive means adapted to extend into the sample quantity during thermal analysis. Spacer means is arranged in the insulating space in the bottom part of the container and/or in the cylindrical part of the container in the vicinity of the bottom part.

17 Claims, 3 Drawing Sheets

(56) References Cited

U.S. PATENT DOCUMENTS

| | | | | |
|---|---|---|---|---|
| 6,269,957 | B1* | 8/2001 | Bowers et al. | 210/473 |
| 6,571,856 | B1* | 6/2003 | Popelar et al. | 164/4.1 |
| 6,604,016 | B1* | 8/2003 | Andersson | 700/204 |
| 2002/0187217 | A1* | 12/2002 | McDonald et al. | 425/547 |
| 2003/0086473 | A1* | 5/2003 | Popelar et al. | 374/139 |
| 2009/0067475 | A1* | 3/2009 | Tavener | 374/208 |
| 2012/0160457 | A1* | 6/2012 | Kim et al. | 165/104.26 |

FOREIGN PATENT DOCUMENTS

| | | |
|---|---|---|
| JP | 55-121395 A | 9/1980 |
| JP | 2001-525540 A | 12/2001 |
| JP | 2002-309689 A | 10/2002 |
| WO | 86/01755 A1 | 3/1986 |
| WO | 92/06809 A1 | 4/1992 |
| WO | 96/23206 A1 | 8/1996 |
| WO | 97/35184 A1 | 9/1997 |

OTHER PUBLICATIONS

Extended European Search Report received for European Patent Application No. 14173594.4, mailed on Sep. 19, 2014, 6 pages.
Office Action received for Swedish Patent Application No. 1350874-2, mailed on Feb. 13, 2014, 6 pages.
Intention to Grant received for Swedish Patent Application No. 1350874-2, mailed on May 28, 2014, 48 pages.

* cited by examiner

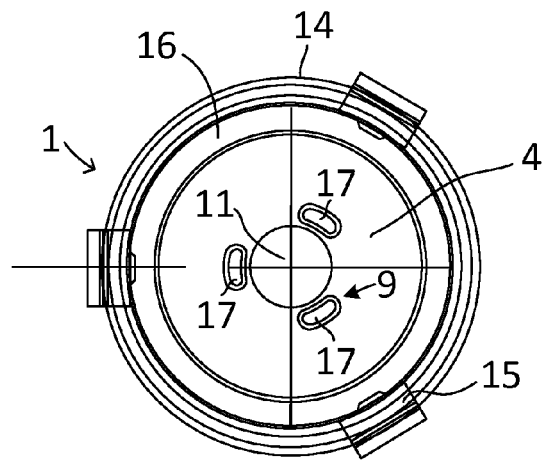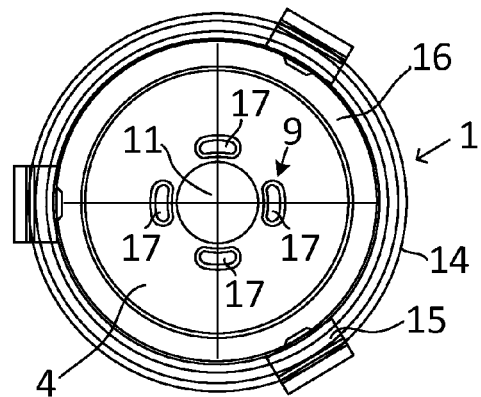
Fig 5a　　　　　　　Fig 6a
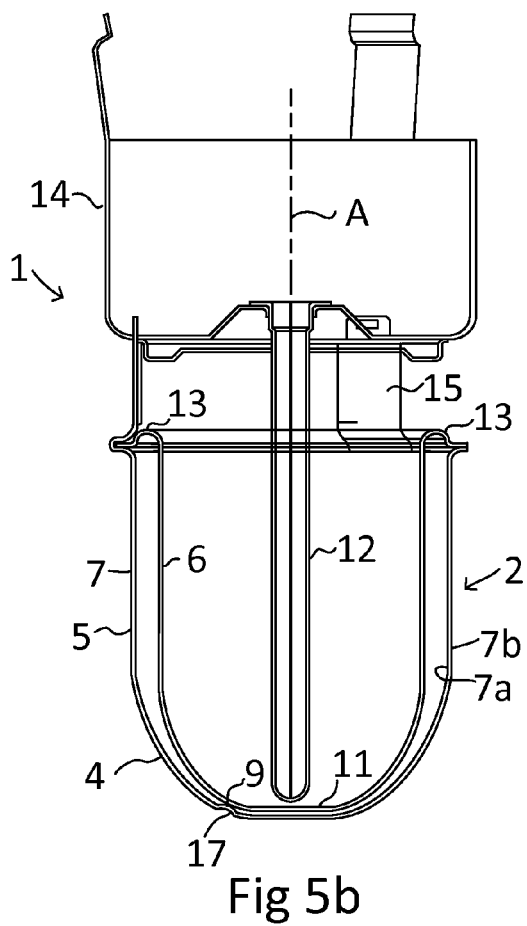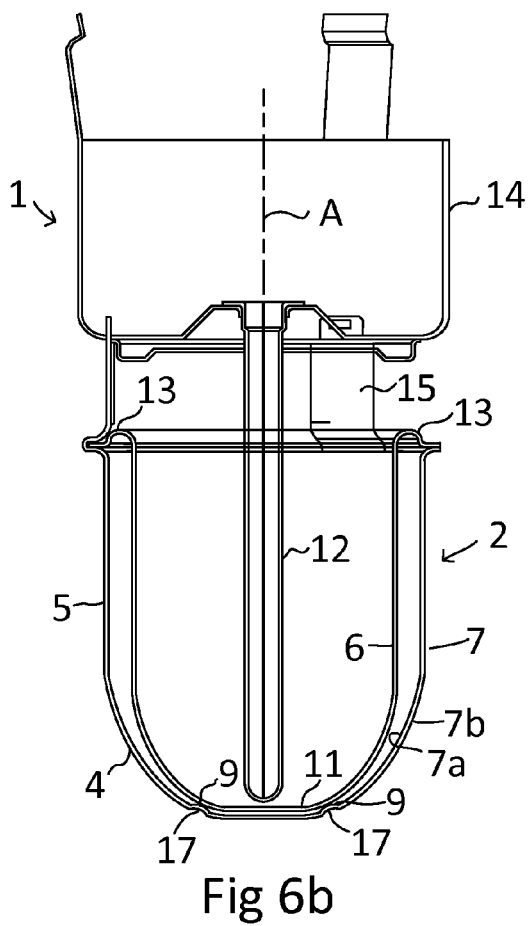
Fig 5b　　　　　　　Fig 6b

SAMPLING DEVICE FOR THERMAL ANALYSIS

REFERENCE TO RELATED APPLICATIONS

This application claims priority from Swedish Patent Application No. 1350874-2, filed on Jul. 12, 2013, the content of which is incorporated herein by reference in its entirety.

FIELD OF THE INVENTION

The present invention relates to a sampling device for thermal analysis of solidifying metal, especially for thermal analysis in the production of castings.

BACKGROUND OF THE INVENTION

Thermal analysis is a technique monitoring variations in temperature change of certain molten substances during solidification to be able to determine the microstructure and hence properties of the substances in solid form. This is accomplished by taking a sample from the melt, transferring it into a sample vessel and recording and evaluating a time-dependent temperature change in the sample during solidification, by means of temperature responsive means, such as thermocouples or other devices known in the art.

When using thermal analysis for controlling solidification processes in molten materials, such as cast-iron or aluminium alloys, a most critical issue is to bring the sample vessel and the sample quantity as close to thermal equilibrium as possible, and to provide for a controlled, even and reproducible rate of heat removal from the sample. The reason for this is to make it possible to measure temperature changes during phase transformations, the knowledge of which is essential in order to control certain solidification processes.

WO 86/01755 discloses a method for producing compacted graphite cast iron by using thermal analysis. A sample is taken from a bath of molten cast iron, and this sample is permitted to solidify during 0.5 to 10 minutes. The temperature is recorded simultaneously by two temperature responsive means, one of which is arranged in the centre of the sample and the other in the immediate vicinity of the vessel wall. So-called cooling curves representing temperature of the iron sample as a function of time are recorded for each of the two temperature responsive means. According to this document it is then possible to determine the necessary amount of structure-modifying agents that must be added to the melt in order to obtain the desired microstructure.

One example of a sampling device is disclosed in WO 96/23206. The device comprises a container intended to contain a sample quantity of liquid metal during analysis, and a sensor for thermal analysis. The container comprises an inner wall with an interior surface intended to face the sample quantity during analysis, and an outer wall with an exterior surface intended to face the ambient atmosphere. The inner and outer walls are joined at the mouth of the container such that an essentially closed space is formed between the walls.

Another example of a sampling device is disclosed in EP 1 034 419. The container of the sampling device comprises a substantially semi-spherical bottom part having a flattened part. The distance between the walls in the flattened part is less than the distance between the walls in the cylindrical part of the container. Thereby, the sampling device simulates a spherical solidification of the molten metal inside the container, which is the most reliable and accurate shape for thermal analysis, but is not spherical in shape.

Thermal analysis is a heat balance. The ultimate shape, and thus the resolution, of the cooling curve is determined by the balance between the heat liberated during solidification and the heat lost to the sampling device and the atmosphere. It is evident that the amount of heat liberated by the solidification of a 200 gram sample of for example cast iron is fixed. If the 200 gram sample is contained in a vessel that cools quickly, the heat liberated by the solidification will be less able to prevail over the heat loss than it would be in a vessel that cools more slowly. The result is that the faster cooling of the vessel will provide less resolution in the cooling curves. Fast cooling caused by the vessel can also alter the true solidification behaviour of the iron by inducing chill or by influencing the undercooling. In order to extract as much information as possible from the heat liberated by the solidification, it is necessary to design a thermal analysis sampling device such that it neither masks nor dilutes the information provided by the solidification. The other major requirement of a thermal analysis sampling device is that it must ensure consistent sampling conditions. Because the differences in the liberated heat between a good microstructure and an out-of-spec microstructure can be very small, it is critical that all variations measured are due to differences in the iron and not due to differences in the sampling technique.

Even though the above mentioned sampling devices work very well for thermal analysis, they are sometimes difficult to produce because the distance between the walls of the container has to be sufficiently regulated in order to ensure the proper heat transfer during thermal analysis such that the sample quantity of the melt in the sampling device solidifies in the intended manner. If the distance between the inner and outer walls of the container is not carefully controlled, the heat transfer, and thus the solidification of the sample quantity, will be affected such that a reliable measurement is jeopardised. Thus, there is still room for an improved sampling device which overcomes or at least reduces the above mentioned problems.

SUMMARY OF THE INVENTION

The object of the invention is a sampling device for thermal analysis which may be easily manufactured in a cost-effective manner and which ensures that reliable results during thermal analysis are achieved.

The object is achieved by a sampling device in accordance with independent claim 1. Embodiments are defined by the dependent claims.

The sampling device according to the present invention ensures that the distance between the inner and outer wall members of the container can be reliably controlled during assembly of the container of the sampling device as well as during operation thereof during thermal analysis. Therefore, the controlled heat loss from the container is ensured during thermal analysis and more reliable measurements by means of the sampling device are enabled. More specifically, the sampling device simulates a spherical solidification of the molten metal inside the container, which is the most reliable, uniform and accurate solidification shape for thermal analysis. The design of the container also influences the convective flow pattern of the metal within the container to produce a flow-separated region at the bottom of the container. This flow pattern and separation can be used to analyse segregated iron at the bottom of the container.

The sampling device according to the invention comprises a container adapted to be immersed into a metal melt and filled with a sample quantity of said metal melt. The container comprises a top part open at the top end thereof, a bottom part adapted to be the first part of the container immersed into the melt when taking a sample quantity, and an essentially cylindrical part arranged between the top part and the bottom part. The container further comprises an inner wall member and an outer wall member. The inner wall member has an inner surface intended to contact a sample quantity of the metal melt during thermal analysis, and an outer surface. The outer wall member has an inner surface, and an outer surface adapted to be exposed to the ambient air during thermal analysis. The inner wall member and the outer wall member are essentially coaxially arranged in the essentially cylindrical part of the container and joined at the top part of the container, and the inner and outer wall members define a closed insulating space between the outer surface of the inner wall member and the inner surface of the outer wall member. The sampling device further comprises temperature responsive means adapted to extend into the sample quantity during thermal analysis. Spacer means is arranged in the insulating space in the bottom part of the container and/or in the essentially cylindrical part of the container in the vicinity of the bottom part.

According to one embodiment, the spacer means constitutes heat conductive wool, preferably metallic wool, such as steel wool.

According to another embodiment, the spacer means constitutes at least one protrusion, preferably at least three protrusions, said protrusion(s) protruding into the insulating closed space from the inner surface of the outer wall member or from the outer surface of the inner wall member. In the case of a plurality of protrusions, at least one protrusion may protrude from the inner surface of the outer wall member and at least one other protrusion may protrude from the outer surface of the inner wall member.

The spacer means preferably provides a thermal short-circuit between the inner wall member and the outer wall member of the container. Thereby, the heat loss of the container is further regulated by improved heat removal from the lower portion of the container and thus, a further improvement of the simulated spherical solidification is achieved.

The spacer means is/are preferably arranged at a distance from the central axis of the container, i.e. they are not present at the very bottom end of the closed space. Thereby, it is further ensured that the distance between the inner and outer wall members, and thus the dimensions of the closed space, can be ensured in a larger portion of the container (compared to a case where a protrusion for example is only present at the central axis of container) and thereby resulting in more reliable results during thermal analysis.

The bottom part of the container is preferably essentially semi-spherical in order to provide the intended simulation of a spherical solidification.

According to one embodiment, the bottom part of the container is essentially semi-spherical and comprises a flattened part arranged at the bottom end thereof and essentially perpendicular to a central axis of the container. The distance between the outer surface of the inner wall member and the inner surface of the outer wall member at the flattened part may suitably be smaller than the distance between the outer surface of the inner wall member and the inner surface of the outer wall member in the essentially cylindrical part of the container. This further improves the heat loss and simulated spherical solidification by balancing the radiation heat loss from the open surface at the top of the container.

According to a further embodiment, the protrusion or protrusions is/are in direct contact with the wall member towards which it/they protrude. That is, if the protrusions protrude from the inner surface of the outer wall member, they are in direct contact with the outer surface of the inner wall member; and if the protrusions protrude from the outer surface of the inner wall member, they are in direct contact with the inner surface of the outer wall member. Thereby, the distance between the inner and outer wall elements are further ensured both during assembly of the container and during use thereof during thermal analysis. Moreover, depending on the material of the protrusion(s), thermal short-circuit between the inner and outer wall members may be enabled.

According to yet another embodiment, the protrusion or protrusions constitute indentations in the outer wall member from the outer surface thereof. Thereby, the container can be easily manufactured for example by stamping the protrusions in the same process step as stamping of the outer wall member.

According to yet another embodiment, the inner wall member comprises an annulus arranged at the top end of the top part of the container, the annulus extending essentially in the axial direction of the container. The annulus inter alia ensures that any excess melt during taking of a sample quantity of the melt does not affect the thermal analysis measurements. Furthermore, the annulus further balances the heat loss between the top and bottom of the container by reducing the radiation heat loss to the atmosphere at the open top of the container.

Preferably, the temperature responsive means comprises at least one temperature responsive sensor arranged in a protective tube arranged essentially coaxially with the cylindrical part of the container along a central axis thereof.

BRIEF DESCRIPTION OF THE DRAWINGS

FIG. 5a illustrates a schematic bottom view of a sampling device according to a forth embodiment.

FIG. 5b illustrates a schematic cross section through a sampling device as shown in FIG. 5a.

FIG. 6a illustrates a schematic bottom view of a sampling device according to a fifth embodiment.

FIG. 6b illustrates a schematic cross section through a sampling device as shown in FIG. 6a.

FIG. 7b illustrates a schematic cross section through a sampling device as shown in FIG. 7a.

DETAILED DESCRIPTION OF THE INVENTION

The invention will be described below with reference to the accompanying drawings. The invention is not limited to the embodiments shown but may be varied within the scope of the appended claims. Moreover, the drawings shall not be considered drawn to scale as some features may be exaggerated in order to more clearly illustrate the features of the sampling device or the container thereof.

Figure 1:
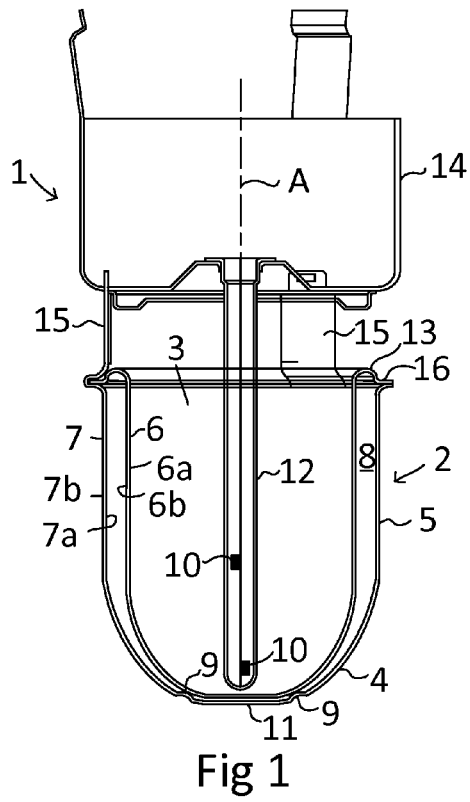
FIG. 1 illustrates a schematic cross section through a sampling device according to a first embodiment.

FIG. 1 illustrates a schematic cross section of a sampling device 1 in accordance with one embodiment of the invention. The sampling device 1 comprises a container 2. The container is intended to be immersed into a melt such that a sample quantity of the melt is allowed to flow into and fill the container. The container, comprising the sample quantity, is then taken out of the melt and thermal analysis is performed. During the thermal analysis, the sample quantity is allowed to solidify and the temperature variation over time is measured using a temperature responsive means 10. The temperature responsive means is suitably positioned by means of a support member 14. The support member 14 may advantageously be located above the top end of the container, preferably concentrically with the central axis A of the container 2.

The container 2 comprises a top part 3 open at the mouth, i.e. open at the top end of the container, a bottom part 4 adapted to be the first part of the container immersed into the melt when taking a sample quantity of the melt, and an essentially cylindrical part 5 arranged between the top part and the bottom part of the container. The container 2 comprises an inner wall member 6 having an inner surface 6a intended to be in contact with the sample quantity, and an outer surface 6b opposite the inner surface 6a. The container further comprises an outer wall member 7 having an inner surface 7a and an opposite outer surface 7b, wherein the outer surface 7b is adapted to be exposed to the ambient atmosphere during thermal analysis.

The inner and outer wall members 6, 7 are essentially coaxially arranged at least in the essentially cylindrical part 5 of the container around the central axis A of the container 2. The inner and outer wall members 6, 7 are arranged at a distance from each other except at the top part of the container where they are joined, for example by welding, crimping or the like. Thereby, a closed space 8 is formed between the inner and outer wall members 6, 7. Thus, the container is a double-walled container.

The inner and outer wall members may suitably each comprise a radially extending flange 16 arranged at the top part 3 of the container 2, the radially extending flanges of the inner and outer wall members being joined together. Thus, the inner and outer wall members are joined at the top end of the container, i.e. at the mouth thereof. The radially extending flanges 16 of the inner and outer wall members extend from the respective inner surface of the wall members outwardly in a direction from the central axis of the container such that they will not disturb the filling of the container during sample taking.

The distance between the inner and outer wall members 6, 7 and thus the dimensions of the closed space 8 is an important parameter in regulating the heat loss due to radiation, convection and thermal conduction. By selecting and fully or partly filling the closed space 8 with a suitable medium, and/or altering the dimensions of the space, it is possible to adapt the geometry and the heat removal rate of the sampling device to the values required for thermal analysis. The closed space 8 may for example be evacuated or filled with gas. It is also plausible to fill the closed space 8 with insulating materials, for example sand or various ceramics, if desired. However, when the closed space is evacuated or filled with gas, such as air, radiation will be an important heat transfer mechanism. As the temperature of the solidifying sample quantity increases, radiation will be of increasing importance since the effect thereof increases with the fourth power of absolute temperature. According to a preferred embodiment, the closed space 8 is filled with air for sake of simplicity and cost.

The bottom part 4 of the container 2 is preferably essentially semi-spherical in shape. Thus, an angle a between a plane P perpendicular to the central axis A of the container and intersecting the central axis A at the very bottom end of the container 2, and an imaginary line L extending from the intersection of said plane P and the central axis A to the outer surface 7b of the outer wall member 7 at the point where the bottom part 4 and the essentially cylindrical part 5 of the container meet, is approximately 45° (see FIG. 8). Suitably, both the inner wall member 6 and the outer wall member 7 of the container 2 are essentially semi-spherical in the bottom part 4 of the container 2.

As shown in FIG. 1, the container 2 may further comprise a flattened part 11 in the bottom part 4 thereof. The flattened part 11 is suitably arranged essentially perpendicular to the central axis A of the container and has an essentially circular form concentric with the central axis of the container. Thus, an angle a between a plane P perpendicular to the central axis A of the container 2 and intersecting the central axis at the very bottom end of the container, and an imaginary line L extending from the intersection of said plane P and the central axis A to the outer surface 7b of the outer wall member 7 at the point where the bottom part 4 and the essentially cylindrical part 5 of the container meet, is less than approximately 45°.

Suitably, both the inner wall member and the outer wall member each comprise a flattened bottom portion as shown for example in FIG. 1.

Moreover, it is preferred that the distance between the inner and outer wall members 6, 7 at the flattened part 11 is smaller than the distance between the inner and outer wall members in the essentially cylindrical part 5 of the container 2. A sampling device comprising such a flattened bottom and the advantages thereof has for example been disclosed in EP 1 034 419, which is hereby incorporated by reference.

The temperature responsive means 10 utilised for thermal analysis of the sample quantity may for example be one or more temperature responsive sensors. Preferably, at least two temperature responsive sensors are used, as shown in FIG. 1. The first temperature responsive sensor is arranged at the close vicinity of the inner wall member 6 of the container such that it is able to measure the temperature curve of the part of the sample quantity which solidifies early in the solidification process of the sample quantity. The second temperature responsive sensor is preferably arranged essentially in the centre of the sample quantity, i.e. essentially in the centre of the container 2 of the sample device, such that it will measure the temperature curve of the part of the sample quantity which solidifies at a late stage of the solidification process of the sample quantity.

More specifically, the shape of the container and the arrangement of the temperature responsive means influence the convective flow pattern of the metal within the container to produce a flow-separated region at the bottom of the container. This flow pattern and separation can be used to analyse segregated metal at the bottom of the container by the arrangement of the temperature responsive means. For example, in order to simulate natural fading of magnesium (which influences the phase transformations of an iron-based melt) which occurs both in a ladle and in a casting, the inner surface of the container may be coated with a reactive material that consumes active magnesium in the melt. The convention currents in the container rinse the sampled iron along the inner surface of the inner wall member and thus cause a low-magnesium iron to accumulate in the stagnant flow-separated region at the bottom of the container. In such a case, the temperature responsive means arranged essentially in the centre may evaluate the non-reacted bulk iron, thus determining the start-of-casting behaviour, while the temperature responsive means arranged close to the inner surface of the inner wall member predicts the end-of-casting behaviour which would occur when casting the iron-based melt.

The temperature responsive sensors are preferably arranged in one or more protective tubes 12. According to one embodiment, two or more temperature responsive sensors are arranged in one protective tube, which in turn is arranged in the sampling device along the central axis of the container and extending into the container such that it will be immersed in the sample quantity during thermal analysis. In such a case, the temperature responsive sensors are arranged inside the protective tube at different locations essentially along the central axis of container as is shown in FIG. 1. It is however possible to arrange temperature responsive sensor(s) in other manners, for example in different protective tubes and at essentially the same distance parallel to the central axis from the top of the container. Also in such an embodiment, a first temperature responsive sensor may suitably be arranged in the close vicinity of the inner surface of the inner wall member whereas a second temperature responsive sensor is arranged essentially in the centre of the sample quantity during thermal analysis.

As shown in FIG. 1, the support member 14 may suitably be attached by legs 15 to the container 2. The number of legs is not limiting to the invention, for example two, three, four or more legs may be used as desired. The legs 15 enable a sample quantity of a melt to easily flow between the legs into the container when the container is immersed in the melt from which the sample quantity shall be taken, thereby enabling an easy and reliable process for filling the container with a consistent sample quantity. Moreover, the support member 14 may preferably act as a lid to reduce radiation heat-loss from the top of the sample quantity during thermal analysis. This further aids in the construction of the sampling device to simulate a spherical solidification of the sample quantity during thermal analysis, because it balances slower heat loss from the bottom of the container due to the construction thereof.

The container 2 of the sampling device according to the present invention further comprises spacer means arranged in the closed space 8 between the inner and outer wall members 6, 7 of the container 2. The spacer means are located in the bottom part 4 of the container 2 and/or in the cylindrical part 5 of the container 2 in the close vicinity of the bottom part 4. Preferably, the spacer means are located only in the bottom part 4 of the container. The purpose of the spacer means is to ensure that the appropriate distance between the inner and outer wall members 6, 7 can be assured during assembly and joining of components of the container 2 during manufacture of the sampling device 1. The spacer means also ensure that inner and outer wall members are kept at a distance from each other during thermal analysis despite the thermal expansion of the inner and outer wall members.

Figure 2:
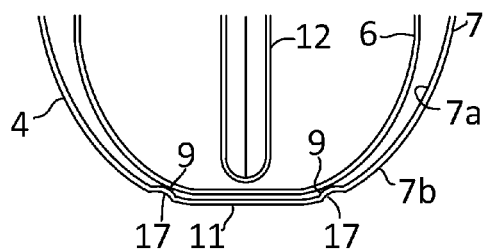
FIG. 2 illustrates an enlargement of a part of the bottom part of a container of the sampling device shown in FIG. 1 in cross section.

In the embodiment shown in FIG. 1, the spacer means constitutes protrusions 9. FIG. 2 is an enlargement of a part of the bottom part of the container shown in FIG. 1 wherein the protrusions 9 can be more clearly seen.

The protrusions preferably provide a thermal short-circuit between the inner and outer wall members 6, 7. Thereby, said spacer means in the form of protrusions also influence the heat loss of the container during thermal analysis increasing the heat loss obtainable through the bottom part of the container. This further improves the simulation of a spherical solidification of the sample quantity inside the container during thermal analysis by further balancing the radiation heat loss from the open surface and thus enables more reliable measurements.

Figure 3:
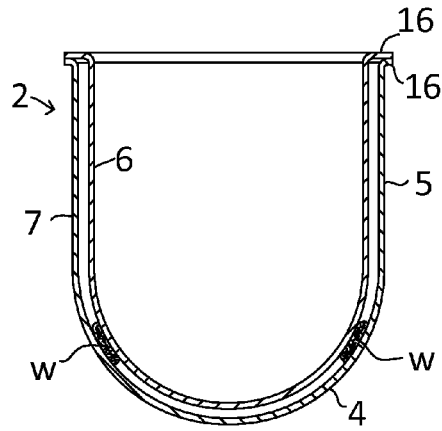
FIG. 3 illustrates a schematic cross section through a container of a sampling device in accordance with a second embodiment.

As shown in FIG. 3, the spacer means need not necessarily be protrusions but may instead be a thermally conductive wool W, such as metallic wool, preferably steel wool. The thermally conductive wool may be located intermittently along a circumferential area within the closed space or be located along the entire circumferential extension, but is in both cases limited in axial extension within the bottom part 4 and/or lower portion of the cylindrical part 5 of the container. The thermally conductive wool W provides a short-circuit between the inner and outer wall members 6, 7. Thus, the thermally conductive wool both ensures the distance between the inner and outer wall members and provides an improved heat loss profile of the container, the heat loss profile simulating a spherical solidification of the sample quantity during thermal analysis.

Figure 4:
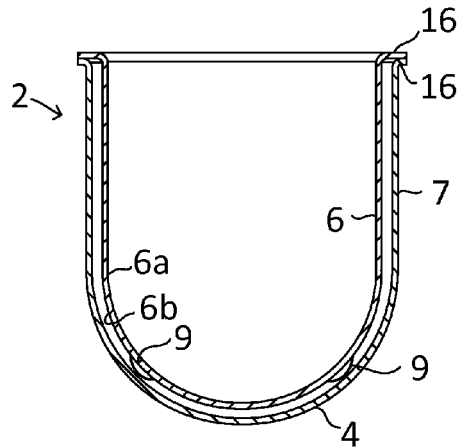
FIG. 4 illustrates a schematic cross section through a container of a sampling device in accordance with a third embodiment.

FIG. 4 illustrates a schematic cross section of a container 2 of a sampling device 1 according to an alternative embodiment. Even though not shown in the figure, the sampling device comprises thermal responsive means as disclosed above, and suitably further comprises a support member 14 and legs 15 attaching the support member to the container in the same manner as disclosed above with reference to FIG. 1. The container as shown in FIG. 4 comprises spacer means in the form of protrusions 9 protruding from the outer surface 6b of the inner wall member 6 towards the inner surface 7a of the outer wall member 7.

According to one embodiment, the spacer means comprises at least two protrusions 9 protruding into the closed space 8 from the inner surface 7a of the outer wall member 7, as shown for example in FIGS. 1 and 2, or from the outer surface 6b of the inner wall member 6, as shown in FIG. 4. Moreover, the protrusions 9 are suitably arranged along a circumference of the inner and/or outer wall members at substantially equal distances from each other. It is preferred that at least three protrusions are arranged in the container to ensure that the intended distance between the inner and outer wall members 6, 7 are kept along the entire circumference thereof. Such an embodiment is shown in FIGS. 5a and 5b, wherein 5a constitutes a bottom view of the sampling device shown in cross section in FIG. 5b. As can be clearly seen in FIG. 5a, three protrusions (which are formed by indentations 17 in the outer wall member of the container 2 which will be described further below) are arranged at a distance from, but close to, the flattened part 11 of the bottom part of the container. Thus, the protrusions 9 are arranged at a radial distance from the central axis A of the container 2. The protrusions 9 are equally spaced around a circumference of the outer wall member 7 of the container 2.

The protrusions 9 may be more than three, such as four, five or more, if desired. FIGS. 6a and 6b illustrate an embodiment wherein the container comprises four protrusions. FIG. 6a constitutes a bottom view of the sampling device shown in cross section in FIG. 6b. As clearly seen in FIG. 6a, four protrusions (formed by indentations 17 in the outer surface of the outer wall member) are arranged in the bottom part 4 of the container 2 at a distance from, but close to, the flattened part 11. The protrusions are equally spaced around a circumference of the outer wall member 7 of the container 2.

Irrespective of the number of protrusions and their placement, the protrusions may be made of the same material as the inner and outer wall members, but may also be made of a different material if desired.

Figure 7A:
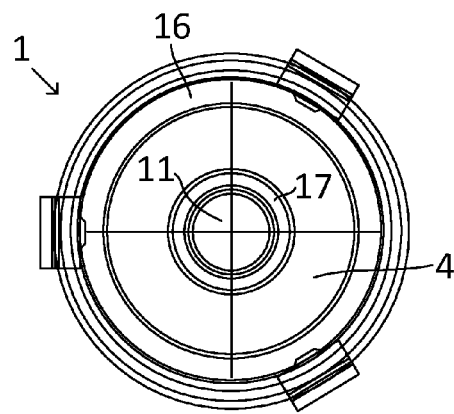
FIG. 7a illustrates a schematic bottom view of a sampling device according a sixth embodiment.
Figure 7B:
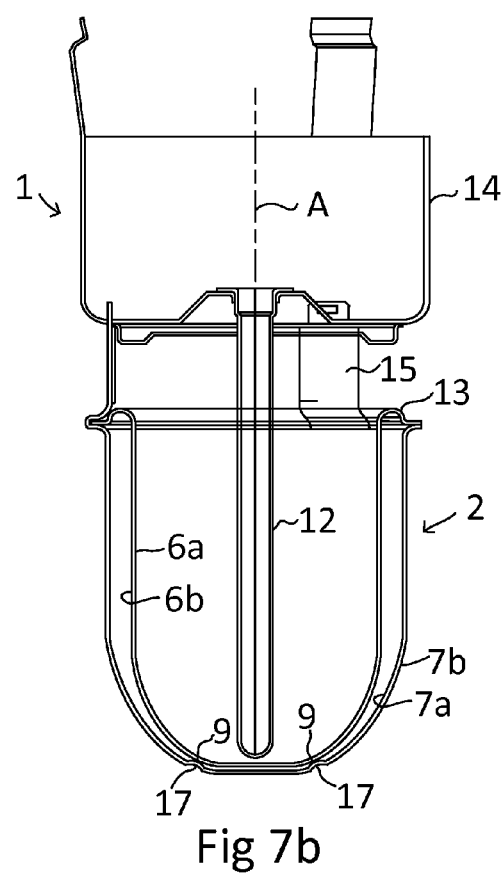

According to another embodiment, the spacer means comprises a single protrusion 9 which protrudes from the inner surface 7a of the outer wall member 7, or from the outer surface 6b of the inner wall member 6 along an entire circumference of said wall member. Thus, such a protrusion is a circumferential protrusion. FIGS. 7a and 7b illustrate such an embodiment, wherein the protrusion 9 protrudes from the inner surface 7b of the outer wall member 7 and has an extension along the entire circumference of the outer wall member 7. FIG. 7a is a bottom view of the sampling device shown in cross section in FIG. 7b.

The protrusion or protrusions are preferably arranged in the bottom part 4 of the container 2 at a radial distance from the central axis A of the container 2 as shown in FIGS. 1-8. In other words, the protrusion or protrusions 9 is/are distanced from the bottom end of the container.

In the embodiment of a container comprising a flattened part 11 in the bottom thereof, the protrusions are suitably arranged at a distance from, however preferably close to, said flattened part, as shown in for example FIGS. 1 and 2.

Preferably, the protrusion or protrusions 9 provide short-circuit between the inner and outer wall members 6, 7 during thermal analysis of a sample quantity in the container 2. This is achieved by selection of an appropriate material of the protrusions, i.e. a thermally conductive material, and ensuring that the protrusions contact the surface of the wall member toward which they protrude. This means that if they protrude from the inner surface of the outer wall member, they contact the outer surface of the inner wall member and vice versa. Thereby, it is possible to further control the heat loss of the container during thermal analysis and simulate a spherical solidification of a sample quantity.

According to one embodiment, the protrusions are present along at least 5%, preferably at least 10% of a circumference of the inner wall member or of the outer wall member from which they protrude. According to another embodiment, the protrusions are present along at most 75%, preferably at most 50%, of a circumference of the inner wall member or of the outer wall member from which they protrude. The axial extension of the protrusions is suitably less than 50%, preferably not more than 30%, more preferably not more than 20%, of the axial extension of the bottom part of the container in order not to influence the heat loss profile of the sampling device negatively.

Even though it is possible to arrange the protrusions either on the outer surface of the inner wall member or on the inner surface of the outer wall member, it is preferred that the protrusions are arranged at the inner surface 7a of the outer wall member 7 as shown for example in FIG. 2. The reason for this is that such a solution facilitates handling of the different components of the container before assembly, mainly because outwardly extending protrusions may be damaged during handling.

For ease of manufacture, the protrusions may suitably constitute indentations 17 in the outer wall member, such as shown in FIGS. 1, 2, 5a, 5b, 6a, 6b, 7a and 7b. The indentations are made from the outer surface 7b of the outer wall member 7, suitably in the same stamping process as the stamping of the outer wall member itself. This may be achieved by designing an appropriate stamping tool.

However, in the case of the protrusions protruding from the outer surface 6b of the inner wall member 6 as shown in FIG. 4, it is not appropriate for the protrusions to constitute indentations in the inner wall member 6. This is because the inner surface 6a of the inner wall member is intended to be in contact with the sample quantity and has to be an essentially smooth surface such that the flow pattern and thus the solidification progress inside the container 2 during thermal analysis is not altered.

The geometrical shape of the protrusions 9 is not limiting to the invention. The protrusions may for example be dome-shaped, essentially cubic or rectangular, oval or kidney-shaped. However, for sake of simplicity during manufacturing, for example when stamped out of the outer wall member, they comprise rounded edges so as not to jeopardise the strength of the container or increase the risk of cracking during stamping.

The inner and outer wall members of the container of the sampling device may for example be made of steel or other suitable material known in the art. The container may optionally be coated with an appropriate coating as previously known in the art. Examples of such coatings may for example be found in WO 92/06809 and WO 97/35184, hereby incorporated by reference.

According to a further embodiment of the sampling device of the invention, the inner wall member comprises an annulus 13 arranged at the top end part 3 of the container 2 as shown in for example FIG. 1. The axial extension of the annulus 13 extends essentially in the axial direction of the container, and the annulus is coaxial with the central axis A of the container 2. The annulus is preferably arranged at the radially extending flange 16 of the inner wall member 6. Moreover, the annulus 13 preferably constitutes a bent part of the flange 16 of the inner wall member. The purpose of the annulus is to ensure that any excess melt readily flows over the annulus during sample taking to ensure that the solidification of the sample quantity inside the container is not affected by possible residual melt present on the flange 16 during thermal analysis. Moreover, the annulus 13 reduces the heat loss at the top part 3 of the container 2 due to a longer heat conduction transportation in the inner wall member 6 before short-circuit of the inner and outer wall members 6, 7 at the joint thereof, and by reducing the thermal communication between the open surface of the sample and the atmosphere to further reduce radiation heat losses.

Figure 8:
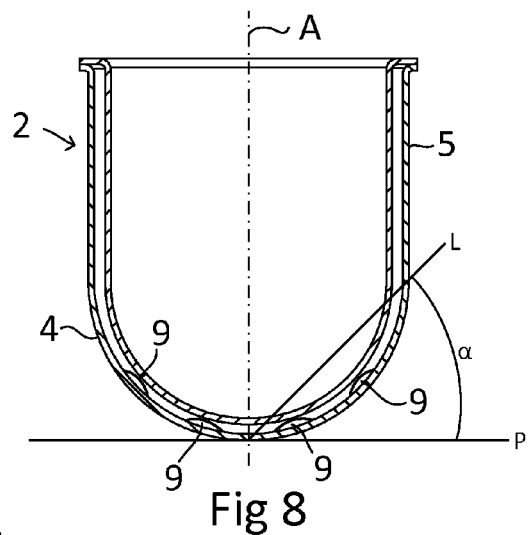
FIG. 8 illustrates a schematic cross section through a container of a sampling device according to a seventh embodiment.

FIG. 8 illustrates a further embodiment wherein a plurality of protrusions 9 are provided on the inner surface 7a of the outer wall member 7 and protruding towards the outer surface of the inner wall member. A first set of protrusions are arranged at a first location in the axial direction of the container and at a first radial distance from the central axis, and a second set of protrusions are arranged at a second location in the axial direction and at a second radial distance from the central axis. The first set of protrusions may be two, three, four or more protrusions. In the same way, the second set may comprise two, three, four or more protrusions. Alternatively, an embodiment wherein the first and/or second set of protrusions is replaced by a circumferential protrusion as disclosed in FIGS. 7a and 7b is plausible. It is also possible that one or more protrusions protrudes from the outer surface of the inner wall member, for example the first set of protrusions may protrude from the inner surface of the outer wall member and the second set of protrusions may extend from the outer surface of the inner wall member without departing from the invention.

The invention is not limited to the specific embodiments described above and shown in the figures. Even though certain features may only have been disclosed in combination with other features of a specific embodiment, the different features described above and shown in the figures may be combined in any possible combination within the scope of the appended claims.

For example, the container shown in any of the FIGS. 1, 5b, 6b and 7b need not have the annulus 13 but can have the configuration of the flanges 16 as shown in FIGS. 3, 4 and 8. In the same way, each of the containers shown in FIGS. 3, 4 and 8 could be provided with an annulus 13 as shown in FIGS. 1, 5b, 6b and 7b.

Moreover, the container shown in any of the FIGS. 1, 5b, 6b and 7b need not have the flattened part 11, but could be essentially semi-spherical as shown in FIGS. 3, 4 and 8. Naturally, the containers shown in FIGS. 3, 4, and 8 could also be provided with a flattened part. If so, the distance between the inner and outer wall members in the flattened part may suitably be less than the distance between the inner and outer wall members in the essentially cylindrical part of the container.

The invention claimed is:

1. Sampling device for thermal analysis of solidifying metal, comprising:
   a container adapted to be immersed into a metal melt and filled with a sample quantity of said metal melt;
   the container comprising a top part open at the top thereof, a bottom part adapted to be the first part of the container immersed into the melt when taking a sample quantity, and a cylindrical part arranged between the top part and the bottom part;
   the container further comprising an inner wall member and an outer wall member;
   the inner wall member having an inner surface adapted to contact a sample quantity of the metal melt during thermal analysis, and an outer surface;
   the outer wall member having an inner surface, and an outer surface adapted to be exposed to the ambient air during thermal analysis;
   wherein the inner wall member and the outer wall member are coaxially arranged in the cylindrical part of the container and joined only at the top part of the container, the inner and outer wall members defining a closed insulating space between the outer surface of the inner wall member and the inner surface of the outer wall member;
   the sampling device further comprising a temperature responsive device adapted to extend into the sample quantity during thermal analysis;
   wherein a spacer is arranged in the insulating space in the bottom part of the container, said spacer being one or more protrusions, said protrusion or protrusions protruding from the inner surface of the outer wall member or from the outer surface of the inner wall member, and
   wherein said spacer is arranged at a radial distance from a central axis of the container.

2. Sampling device according to claim 1, wherein said spacer provides a thermal short-circuit between the inner wall member and the outer wall member.

3. Sampling device according to claim 1, wherein the bottom part of the container is semi-spherical.

4. Sampling device according to claim 1, wherein the bottom part of the container is semi-spherical and comprises a flattened part arranged at the bottom end thereof and perpendicular to a central axis of the container.

5. Sampling device according to claim 4, wherein the distance between the outer surface of the inner wall member and the inner surface of the outer wall member at the flattened part is smaller than the distance between the outer surface of the inner wall member and the inner surface of the outer wall member in the cylindrical part of the container.

6. Sampling device according to claim 1, wherein said protrusion or protrusions are in direct contact with a surface of the wall member toward which they protrude.

7. Sampling device according to claim 1, wherein said spacer comprises at least three protrusions, said protrusions protruding from the inner surface of the outer wall member and/or from the outer surface of the inner wall member.

8. Sampling device according to claim 7, wherein said protrusions are arranged along a circumference of the inner wall member or the outer wall member at substantially equal distances from each other.

9. Sampling device according to claim 1, wherein said protrusion or protrusions constitute an indentation or indentations in the outer wall member arranged in the outer surface thereof.

10. Sampling device according to claim 1, wherein the inner wall member comprises an annulus arranged at the top end of the top part of the container, the annulus extending in the axial direction of the container.

11. Sampling device according to claim 1, wherein said temperature responsive device comprises at least one temperature responsive sensor arranged in a protective tube arranged coaxially with the cylindrical part of the container along a central axis thereof.

12. Sampling device for thermal analysis of solidifying metal, comprising:
   a container adapted to be immersed into a metal melt and filled with a sample quantity of said metal melt;
   the container comprising a top part open at the top thereof, a bottom part adapted to be the first part of the container immersed into the melt when taking a sample quantity, and a cylindrical part arranged between the top part and the bottom part;
   the container further comprising an inner wall member and an outer wall member;
   the inner wall member having an inner surface intended to contact a sample quantity of the metal melt during thermal analysis, and an outer surface;
   the outer wall member having an inner surface, and an outer surface adapted to be exposed to the ambient air during thermal analysis;
   wherein the inner wall member and the outer wall member are coaxially arranged in the cylindrical part of the container and joined at the top part of the container, the inner and outer wall members defining a closed insulating space between the outer surface of the inner wall member and the inner surface of the outer wall member;
   the sampling device further comprising a temperature responsive device adapted to extend into the sample quantity during thermal analysis;
   wherein a spacer is arranged in the insulating space in the bottom part of the container and/or in the cylindrical part of the container in the vicinity of the bottom part, said spacer being a heat conductive wool, wherein the heat conductive wool is radially distanced from a central axis of the container and has an axial extension limited within the bottom part of the container and/or lower portion of the cylindrical part of the container.

13. Sampling device according to claim 12, wherein said heat conductive wool is a metal wool.

14. Sampling device according to claim 12, wherein said spacer provides a thermal short-circuit between the inner wall member and the outer wall member.

15. Sampling device according to claim 12, wherein the bottom part of the container is semi-spherical and comprises a flattened part arranged at the bottom end thereof and perpendicular to a central axis of the container.

16. Sampling device according to claim 14, wherein the distance between the outer surface of the inner wall member and the inner surface of the outer wall member at the flattened part is smaller than the distance between the outer surface of the inner wall member and the inner surface of the outer wall member in the cylindrical part of the container.

17. Sampling device for thermal analysis of solidifying metal, comprising:
- a container adapted to be immersed into a metal melt and filled with a sample quantity of said metal melt;
- the container comprising a top part open at the top thereof, a bottom part adapted to be the first part of the container immersed into the melt when taking a sample quantity, and a cylindrical part arranged between the top part and the bottom part;
- the container further comprising an inner wall member and an outer wall member;
- the inner wall member having an inner surface intended to contact a sample quantity of the metal melt during thermal analysis, and an outer surface;
- the outer wall member having an inner surface, and an outer surface adapted to be exposed to the ambient air during thermal analysis;
- wherein the inner wall member and the outer wall member are coaxially arranged in the cylindrical part of the container and joined only at the top part of the container, the inner and outer wall members defining a closed insulating space between the outer surface of the inner wall member and the inner surface of the outer wall member;
- the sampling device further comprising a temperature responsive device adapted to extend into the sample quantity during thermal analysis;
- wherein a spacer is arranged in the insulating space in the cylindrical part of the container in the vicinity of the bottom part, said spacer being one or more protrusions protruding from the inner surface of the outer wall member, said one or more protrusions constituting one or more indentations in the outer wall member arranged in the outer surface of the outer wall member.

* * * * *